(12) United States Patent
Ohtsuka et al.

(10) Patent No.: US 10,851,031 B2
(45) Date of Patent: Dec. 1, 2020

(54) METHOD FOR MANUFACTURING DIFLUOROMETHYLENE COMPOUND

(71) Applicant: DAIKIN INDUSTRIES, LTD., Osaka (JP)

(72) Inventors: Tatsuya Ohtsuka, Osaka (JP); Yoshichika Kuroki, Osaka (JP); Atsushi Shirai, Osaka (JP); Moe Hosokawa, Osaka (JP); Yosuke Kishikawa, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 16/471,975

(22) PCT Filed: Dec. 22, 2017

(86) PCT No.: PCT/JP2017/046195
§ 371 (c)(1),
(2) Date: Jun. 20, 2019

(87) PCT Pub. No.: WO2018/123890
PCT Pub. Date: Jul. 5, 2018

(65) Prior Publication Data
US 2020/0087230 A1 Mar. 19, 2020

(30) Foreign Application Priority Data

Dec. 26, 2016 (JP) ................................ 2016-251315
Nov. 13, 2017 (JP) ................................ 2017-218128

(51) Int. Cl.
*C07C 17/18* (2006.01)
*C07C 67/307* (2006.01)

(52) U.S. Cl.
CPC ............ *C07C 17/18* (2013.01); *C07C 67/307* (2013.01); *C07C 2601/14* (2017.05)

(58) Field of Classification Search
CPC .... C07C 17/18; C07C 67/307; C07C 2601/14
See application file for complete search history.

(56) References Cited

U.S. PATENT DOCUMENTS 2,859,245 A * 11/1958 Smith ..................... C07B 39/00
562/853
3,848,064 A * 11/1974 Becher et al. ......... C01B 17/453
423/469
7,265,247 B1 9/2007 Umemoto et al.

FOREIGN PATENT DOCUMENTS

CN 102107857 5/2012
EP 1304316 4/2003

OTHER PUBLICATIONS

Sulfur choride-Wikipedia, Wikipedia ,2015, p. 1, recovered from https://en.wikipedia.org/wiki/Sulfur_chloride on Feb. 19, 2020 (Year: 2015).*
Zaragoza Dorwald, Side Reactions in Organic Synthesis, 2005, Wiley-Vch Verlag GmbH & Co. KGaA, Weinheim, Preface. p. IX. (Year: 2005).*
International Search Report dated Mar. 27, 2018 in International (PCT) Application No. PCT/JP2017/046195.
Hasek et al., "The Chemistry of Sulfur Tetrafluoride. II. The Fluorination of Organic Carbonyl Compounds", Journal of the American Chemical Society, vol. 82, No. 3, 1960, pp. 543-551.
Middleton et al., "New Fluorinating Reagents. Dialkylaminosulfur Fluorides", The Journal of Organic Chemistry, vol. 40, No. 5, 1975, pp. 574-578.
Lal et al., "Bis(2-methoxyethyl)aminosulfur trifluoride: a new broad-spectrum deoxofluorinating agent with enhanced thermal stability", Chemical Communications, 1999, pp. 215-216.
Hara et al., "IF$_5$-pyridine-HF: air- and moisture-stable fluorination reagent", Tetrahedron, vol. 68, No. 49, 2012, pp. 10145-10150.
Umemoto et al., "Discovery of 4-tert-Butyl-2,6-dimethylphenylsulfur Trifluoride as a Deoxofluorinating Agent with High Thermal Stability as Well as Unusual Resistance to Aqueous Hydrolysis, and Its Diverse Fluorination Capabilities Including Deoxofluoro-Arylsulfinylation with High Stereoselectivity", J. Am. Chem. Soc., vol. 132, No. 51, 2010, pp. 18199-18205.
Lau et al., "The Reaction of Chlorine Monofluoride with Selenium Dioxide, Tetrachloride and Sulphur Tetrachloride", Journal of Fluorine Chemistry, 1975, vol. 6, No. 1, pp. 77-81.
Boswell et al., "Fluorination by Sulfur Tetrafluoride", Organic Reactions, 2011, pp. 1-124.
Extended Search Report dated Jul. 28, 2020 in corresponding European Patent Application No. 17886363.5.

* cited by examiner

Primary Examiner — Paul A Zucker
(74) Attorney, Agent, or Firm — Wenderoth, Lind & Ponack, L.L.P.

(57) ABSTRACT

The problem to be solved by the present invention is to provide a novel method for producing a difluoromethylene compound. This problem is solved by a method for producing a difluoromethylene compound containing a —$CF_2$— moiety, the method comprising step A of mixing:
a) a carbonyl compound containing a —C(O)— moiety;
b) optionally an amine;
c) a fluoride represented by the formula: MF, wherein M represents a Group 1 element of the periodic table;
d) a halogenated fluorine compound represented by the formula: $XF_n$, wherein X represents chlorine, bromine, or iodine, and n is a natural number of 1 to 5; and
e) sulfur chloride.

11 Claims, No Drawings

METHOD FOR MANUFACTURING DIFLUOROMETHYLENE COMPOUND

TECHNICAL FIELD

The present invention relates to a method for producing a difluoromethylene compound.

BACKGROUND ART

Compounds having a difluoromethylene skeleton (i.e., difluoromethylene compounds) are useful as a liquid crystal material, a medicinal drug, an intermediate thereof, etc. Although studies have been made on various production methods, deoxyfluorination of carbonyl compound, in particular, is a useful reaction. Fluorinating agents known to be suitable for such a reaction include sulfur tetrafluoride (SF4), N,N-diethylaminosulfur trifluoride (DAST), bis(methoxymethyl)aminosulfur trifluoride (Deoxo-Fluor, trade name), substituted phenylsulfur trifluoride (Fluolead, trade name), and the like.

However, SF4 is highly toxic and is in the form of gas; thus, it is difficult to handle and obtain. DAST and Deoxofluor are liquids that have low thermal stability and generate a very large amount of thermal energy when decomposed. In particular, DAST is explosive and requires caution when handled. Although Fluolead is highly stable, there is a problem in that sulfur compounds produced as a byproduct by decomposition of a fluorinating agent are not easily separated from the reaction product.

CITATION LIST

Patent Literature

PTL 1: U.S. Pat. No. 7,265,247

Non-Patent Literature

NPL 1: J. Am. Chem. Soc., 82, and 543 (1960)
NPL 2: J. Org. Chem., 40, and 574 (1975)
NPL 3: Chemical Communications 215 (1999)

SUMMARY OF INVENTION

Technical Problem

An object of the present invention is to provide a novel method for producing a difluoromethylene compound, in particular, a simple method for producing a difluoromethylene compound.

Solution to Problem

As a result of extensive research, the present inventors found that the above problem can be solved by a production method comprising step A of mixing:
a) a carbonyl compound containing a —C(O)— moiety;
b) optionally an amine;
c) a fluoride represented by the formula: MF (wherein M represents a Group 1 element of the periodic table);
d) a halogenated fluorine compound represented by the formula: $XF_n$ (wherein X represents chlorine, bromine, or iodine, and n is a natural number of 1 to 5); and
e) sulfur chloride.

The present invention has been accomplished based on this finding.

The present invention encompasses the following embodiments.

Item 1. A method for producing a difluoromethylene compound containing a —$CF_2$— moiety, the method comprising step A of mixing:
a) a carbonyl compound containing a —C(O)— moiety;
b) optionally an amine;
c) a fluoride represented by the formula: MF, wherein M represents a Group 1 element of the periodic table; d) a halogenated fluorine compound represented by the formula: $XF_n$, wherein X represents chlorine, bromine, or iodine, and n is a natural number of 1 to 5; and
e) sulfur chloride.

Item 2. The production method according to Item 1, wherein the difluoromethylene compound containing a —$CF_2$— moiety is a difluoromethylene compound represented by formula (1):

$$R^{11}\text{—}CF_2\text{—}R^{12} \qquad (1)$$

wherein
$R^{11}$ represents $R^{21}$ or fluorine,
$R^{12}$ represents $R^{22}$ or fluorine,
$R^{21}$ and $R^{22}$ are identical or different, and each represents
(a) hydrogen,
(b) hydroxyl, or
(c) an organic group, or
$R^{21}$ and $R^{22}$, taken together with the —$CF_2$— moiety to which they are attached, may form a ring,
with the proviso that
(i) neither $R^{11}$ nor $R^{12}$ is hydroxyl, and
(ii) neither $R^{11}$ nor $R^{12}$, and neither $R^{21}$ nor $R^{22}$, is an organic group bonded via —O—, and that
a) the carbonyl compound is a carbonyl compound represented by formula (2):

$$R^{21}\text{—}C(O)\text{—}R^{22} \qquad (2),$$

wherein the symbols in the formula are as defined above.

Item 3. The production method according to Item 1 or 2, wherein d) the halogenated fluorine compound is $IF_5$.

Item 4. The production method according to any one of Items 1 to 3, wherein the method comprises mixing b) the amine and c) the fluoride.

Item 5. The production method according to Item 4, wherein b) the amine and c) the fluoride are used in the form of a salt of b) the amine and c) the fluoride.

Item 6. The production method according to any one of Items 1 to 5, wherein b) the amine, c) the fluoride, and d) the halogenated fluorine compound are used in the form of a complex of b) the amine, c) the fluoride, and d) the halogenated fluorine compound.

Item 7. The production method according to any one of Items 1 to 6, wherein c) the fluoride is HF.

Item 8. The production method according to any one of Items 1 to 7, wherein step A comprises:
step A1 of reacting d) the halogenated fluorine compound with e) the sulfur chloride; and
step A2 of reacting a) the carbonyl compound with a reaction product of step A1.

Item 9. The production method according to Item 8, wherein step A1 and step A2 are performed in one pot.

Item 10. The production method according to Item 9, wherein step A1 and step A2 are performed sequentially.

Item 11. The production method according to Item 9, wherein step A1 and step A2 are performed simultaneously.

Advantageous Effects of Invention

The present invention provides a novel method for producing a difluoromethylene compound, in particular, a simple, efficient method for producing a difluoromethylene compound.

DESCRIPTION OF EMBODIMENTS

Term

The symbols and the abbreviations in this specification are to be interpreted as having the general meanings in the related technical field to which the present invention pertains, according to the context of this specification, unless otherwise specified.

In this specification, the term "comprise" or "contain" is intended to encompass the meanings of "consist essentially of" and "consist of."

The steps, treatments, or operations in this specification can be performed at room temperature, unless otherwise specified.

In this specification, room temperature refers to a temperature of 10 to 40° C.

In this specification, the term "$C_n$-$C_m$" (wherein n and m are numbers) indicates that the carbon number is n or more and m or less, as usually would be understood by a person skilled in the art.

In this specification, examples of "non-aromatic hydrocarbon ring" include $C_3$-$C_8$ non-aromatic hydrocarbon rings. Specific examples include:
(1) $C_3$-$C_8$ cycloalkanes, such as cyclopropane, cyclobutane, cyclopentane, cyclohexane, cycloheptane, and cyclooctane;
(2) $C_5$-$C_8$ cycloalkenes, such as cyclopentene, cyclohexene, cycloheptene, and cyclooctene;
(3) $C_5$-$C_8$ cycloalkadienes, such as cyclopentadiene, cyclohexadiene, cycloheptadiene, and cyclooctadiene;
(4) $C_5$-$C_8$ bridged-ring hydrocarbons, such as bicyclo[2.1.0]pentane, bicyclo[2.2.1]heptane, bicyclo[3.2.1]octane, bicyclo[2.2.1]hept-2-ene, and tricyclo[2.2.1.0]heptane; and the like.

In this specification, examples of "non-aromatic heterocycle" include 3- to 8-membered non-aromatic heterocycles and the like. Specific examples include oxirane, azetidine, oxetane, thietane, pyrrolidine, dihydrofuran, tetrahydrofuran, tetrahydrothiophene, imidazolidine, oxazolidine, isoxazoline, piperidine, dihydropyran, tetrahydropyran, tetrahydrothiopyran, morpholine, thiomorpholine, piperazine, dihydrooxazine, tetrahydrooxazine, dihydropyrimidine, tetrahydropyrimidine, azepane, oxepane, thiepane, oxazepane, thiazepane, azocane, oxocane, thiocane, oxazocane, thiazocane, and the like.

In this specification, the term "organic group" refers to a group containing at least one carbon atom, or a group formed by removing one hydrogen atom from an organic compound.

Examples of the "organic group" include hydrocarbon optionally having at least one substituent, non-aromatic heterocyclic group optionally having at least one substituent, heteroaryl optionally having at least one substituent,
cyano,
aldehyde,
RO—,
RCO—,
RSO$_2$—,
ROCO—, and
ROSO$_2$—, wherein Rs are each independently
hydrocarbon optionally having at least one substituent,
non-aromatic heterocyclic group optionally having at least one substituent, or
heteroaryl optionally having at least one substituent.

In this specification, examples of "hydrocarbon" include alkyl, alkenyl, alkynyl, cycloalkyl, cycloalkenyl, cycloalkadienyl, aryl, aralkyl, and groups of combinations thereof.

In this specification, "(cyclo)alkyl" refers to alkyl and/or cycloalkyl.

In this specification, examples of "alkyl" include linear or branched $C_1$-$C_{10}$ alkyl, such as methyl, ethyl, propyl, isopropyl, butyl, isobutyl, sec-butyl, tert-butyl, pentyl, isopentyl, neopentyl, hexyl, heptyl, octyl, nonyl, and decyl, unless otherwise specified.

In this specification, examples of "alkenyl" include linear or branched $C_2$-$C_{10}$ alkenyl, such as vinyl, 1-propen-1-yl, 2-propen-1-yl, isopropenyl, 2-buten-1-yl, 4-penten-1-yl, and 5-hexen-1-yl, unless otherwise specified.

In this specification, examples of "alkynyl" include linear or branched $C_2$-$C_{10}$ alkynyl, such as ethynyl, 1-propyn-1-yl, 2-propyn-1-yl, 4-pentyn-1-yl, and 5-hexyne-1-yl, unless otherwise specified.

In this specification, examples of "cycloalkyl" include $C_3$-$C_7$ cycloalkyl, such as cyclopropyl, cyclobutyl, cyclopentyl, cyclohexyl, and cycloheptyl, unless otherwise specified.

In this specification, examples of "cycloalkenyl" include $C_3$-$C_7$ cycloalkenyl, such as cyclopropenyl, cyclobutenyl, cyclopentenyl, cyclohexenyl, and cycloheptenyl, unless otherwise specified.

In this specification, examples of "cycloalkadienyl" include $C_4$-$C_{10}$ cycloalkadienyl, such as cyclobutadienyl, cyclopentadienyl, cyclohexadienyl, cycloheptadienyl, cyclooctadienyl, cyclononadienyl, and cyclodecadienyl, unless otherwise specified.

In this specification, "aryl" may be monocyclic, bicyclic, tricyclic, or tetracyclic, unless otherwise specified.

In this specification, "aryl" may be $C_6$-$C_{18}$ aryl, unless otherwise specified.

In this specification, examples of "aryl" include phenyl, 1-naphthyl, 2-naphthyl, 2-biphenyl, 3-biphenyl, 4-biphenyl, and 2-anthryl, unless otherwise specified.

In this specification, examples of "aralkyl" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl, unless otherwise specified.

In this specification, "non-aromatic heterocyclic group" may be monocyclic, bicyclic, tricyclic, or tetracyclic, unless otherwise specified.

In this specification, "non-aromatic heterocyclic group" may be, for example, a non-aromatic heterocyclic group containing, in addition to carbon, 1 to 4 heteroatoms selected from oxygen, sulfur, and nitrogen as a ring-constituting atom or ring-constituting atoms, unless otherwise specified.

In this specification, "non-aromatic heterocyclic group" may be saturated or unsaturated, unless otherwise specified.

In this specification, examples of "non-aromatic heterocyclic group" include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, dihydroquinolyl, and the like, unless otherwise specified.

In this specification, examples of "heteroaryl" include 5- or 6-membered monocyclic aromatic heterocyclic groups, 5- to 10-membered aromatic fused heterocyclic groups, and the like, unless otherwise specified.

In this specification, examples of "5- or 6-membered monocyclic aromatic heterocyclic group" include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), pyrazinyl, and the like, unless otherwise specified.

In this specification, examples of "5- to 10-membered aromatic fused heterocyclic group" include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl), and the like, unless otherwise specified.

In this specification, examples of "halogen atom" include fluorine, chlorine, bromine, and iodine, unless otherwise specified.

In this specification, examples of the term "halogenated" can include the meanings of chlorinated, brominated, and iodinated, unless otherwise specified.

Production Method

A method for producing a difluoromethylene compound containing a —$CF_2$— moiety (in this specification, sometimes simply referred to as "the difluoromethylene compound") according to the present invention comprises step A of mixing:

a) a carbonyl compound containing a —C(O)— moiety (in this specification, sometimes referred to as "a) the carbonyl compound");

b) optionally an amine;

c) a fluoride represented by the formula: MF, wherein M represents a Group 1 element of the periodic table (in this specification, sometimes referred to as "c) the fluoride");

d) a halogenated fluorine compound represented by the formula: $XF_n$, wherein X represents chlorine, bromine, or iodine, and n is a natural number of 1 to 5 (in this specification, sometimes referred to as "d) the halogenated fluorine compound"); and e) sulfur chloride.

Just to note, the term "difluoromethylene" in the difluoromethylene compound produced by the production method of the present invention refers to the —$CF_2$— moiety.

The difluoromethylene compound can contain one or more —$CF_2$— moieties, and corresponding to this, a) the carbonyl compound can contain one or more —C(O)— moieties.

a) The carbonyl compound used in the production method of the present invention is converted in step A into a difluoromethylene compound containing a —$CF_2$— moiety.

It is preferable that a compound in which an organic group is bonded to the —C(O)— moiety via —O— (i.e., an ester compound) is excluded from a) the carbonyl compound, which is a reaction starting compound.

Accordingly, it is preferable that a compound in which an organic group is bonded to the —$CF_2$— moiety via —O— is excluded from the difluoromethylene compound, i.e., the reaction product.

Just to note, the —$CF_2$— moiety in the difluoromethylene compound, i.e., the reaction product, may be, for example, part of a —$CF_3$ group. That is, the difluoromethylene compound may be a trifluoromethyl compound.

In regard to this, when —COOH is attached to the —C(O)— moiety in a) the carbonyl compound, the —C(O)—COOH moiety can be converted into a —$CF_3$ group in step A. Therefore, in this case, a trifluoromethyl compound is produced by the production method of the present invention.

The difluoromethylene compound produced by the production method of the present invention is preferably represented by formula (1):

$$R^{11}-CF_2-R^{12} \tag{1}$$

wherein
R$^{11}$ represents R$^{21}$ or fluorine,
R$^{12}$ represents R$^{22}$ or fluorine,
R$^{21}$ and R$^{22}$ are identical or different and each represents
(a) hydrogen,
(b) hydroxyl, or
(c) an organic group, or
R$^{21}$ and R$^{22}$ may be attached to each other,
with the proviso that
(i) neither R$^{11}$ nor R$^{12}$ is hydroxyl, and
(ii) neither R$^{11}$ nor R$^{12}$, and neither R$^{21}$ nor R$^{22}$, is an organic group bonded via —O—.

Corresponding to this preferable difluoromethylene compound, a) the carbonyl compound is preferably a carbonyl compound represented by formula (2):

$$R^{21}\text{—C(O)—}R^{22} \qquad (2),$$

wherein the symbols in the formula are as defined above.

R$^{11}$ in formula (1) representing the target compound corresponds to R$^{21}$ in formula (2) representing a reaction starting compound, and R$^{11}$ and R$^{21}$ may represent the same.

R$^{12}$ in formula (1) representing the target compound corresponds to R$^{22}$ in formula (2) representing a reaction starting compound, and R$^{12}$ and R$^{22}$ may represent the same.

However, as is understood from the description above, in the production method according to this embodiment, when R$^{21}$ in formula (2) above is —COOH, R$^{11}$ in formula (1) may be fluorine.

Similarly, in the production method according to this embodiment, when R$^{22}$ in formula (2) above is —COOH, R$^{12}$ in formula (1) may be fluorine.

The organic group represented by R$^{11}$ is preferably hydrocarbon optionally having at least one substituent. (This hydrocarbon may contain at least one moiety selected from the group consisting of —NR—, =N—, —N=, —O—, and —S—, wherein R represents hydrogen or an organic group.)

The "hydrocarbon" in the "hydrocarbon optionally having at least one substituent" is preferably C$_1$-C$_{30}$ hydrocarbon, more preferably C$_1$-C$_{20}$ hydrocarbon, and still more preferably C$_1$-C$_{10}$ hydrocarbon.

The hydrocarbon is preferably alkyl or aryl, and more preferably C$_1$-C$_{10}$ alkyl or C$_6$-C$_{20}$ aryl.

The hydrocarbon (including alkyl and aryl) may contain at least one moiety selected from the group consisting of —NR— (wherein R represents hydrogen or an organic group), =N—, —N=, —O—, and —S—.

This moiety may be inserted in the carbon-carbon bonding of the hydrocarbon and/or inserted adjacent to the —CF$_2$— moiety in formula (1) (and corresponding to this, adjacent to the —C(O)— moiety in formula (2)).

The organic group represented by R in the —NR— moiety is preferably hydrocarbon optionally having at least one substituent, and the hydrocarbon in the "hydrocarbon optionally having at least one substituent" is preferably C$_1$-C$_{30}$ hydrocarbon, more preferably C$_1$-C$_{20}$ hydrocarbon, and still more preferably C$_1$-C$_{10}$ hydrocarbon.

The organic group represented by R$^{12}$ is preferably hydrocarbon optionally having at least one substituent. (This hydrocarbon may contain at least one moiety selected from the group consisting of —NR—, =N—, —N=, —O—, and —S—, wherein R represents hydrogen or an organic group.)

The "hydrocarbon" in the "hydrocarbon optionally having at least one substituent" is preferably C$_1$-C$_{30}$ hydrocarbon, more preferably C$_1$-C$_{20}$ hydrocarbon, and still more preferably C$_1$-C$_{10}$ hydrocarbon.

The hydrocarbon is preferably alkyl or aryl, and more preferably C$_1$-C$_{10}$ alkyl or C$_6$-C$_{20}$ aryl.

The hydrocarbon (including alkyl and aryl) may contain at least one moiety selected from the group consisting of —NR— (wherein R represents hydrogen or an organic group), =N—, —N=, —O—, and —S—.

This moiety may be inserted in the carbon-carbon bonding of the hydrocarbon and/or inserted adjacent to the —CF$_2$— moiety in formula (1).

The organic group represented by R in R$^{12}$ is preferably hydrocarbon optionally having at least one substituent, and the hydrocarbon in the "hydrocarbon optionally having at least one substituent" is preferably C$_1$-C$_{20}$ hydrocarbon, more preferably C$_1$-C$_{10}$ hydrocarbon, and still more preferably C$_1$-C$_5$ hydrocarbon.

Just to note, as a person skilled in the art would usually understand, aryl containing at least one moiety selected from the group consisting of —NR—, =N—, —N=, —O—, and —S— may be heteroaryl.

Examples of the "substituent" in the "hydrocarbon optionally having at least one substituent" represented by R$^{11}$ or R$^{21}$ include halogen atoms, nitro, cyano, oxo, thioxo, sulfo, sulfamoyl, sulfinamoyl, and sulfenamoyl.

The numbers of the substituents in R$^{11}$ and R$^{21}$ may be the same or different and within a range of one to the maximum replaceable number (e.g., one, two, three, four, five, or six).

It is preferable that the ring formed by R$^{11}$ and R$^{21}$, taken together with the —CF$_2$— moiety to which R$^{11}$ and R$^{21}$ are attached, be a 3- to 8-membered ring optionally further having at least one substituent, in addition to fluorine in the —CF$_2$— moiety.

The ring may be a monocyclic, fused, or spiro ring.

The ring may be a non-aromatic hydrocarbon ring or non-aromatic heterocycle.

Examples of the substituent include halogen atoms, nitro, cyano, oxo, thioxo, sulfo, sulfamoyl, sulfinamoyl, and sulfenamoyl.

The number of the substituents may be within a range of one to the maximum replaceable number (e.g., one, two, three, four, five, or six).

Just to note, the "organic group bonded via —O—" excluded from R$^{21}$ and R$^{22}$ is, for example, hydrocarbyloxy optionally having at least one substituent.

Examples of b) the amine include aliphatic amines (primary amine, secondary amine, tertiary amine), alicyclic amines (secondary amine, tertiary amine), aromatic amines (primary amine, secondary amine, tertiary amine), heterocyclic amines, and like organic bases; polyaryl amine, polyvinylpyridine, and like polymers carrying amine compounds; and the like.

In this specification, examples of aliphatic primary amines include methylamine, ethylamine, propylamine, butylamine, pentylamine, hexylamine, cyclohexylamine, ethylenediamine, and the like.

In this specification, examples of aliphatic secondary amines include dimethylamine, diethylamine, dipropylamine, dibutylamine, dipentylamine, dihexylamine, dicyclohexylamine, and the like.

In this specification, examples of aliphatic tertiary amines include trimethylamine, triethylamine, diisopropylethylamine, N,N,N',N'-tetramethylethylenediamine, and the like.

In this specification, examples of alicyclic secondary amines include piperidine, piperazine, pyrrolidine, morpholine, and the like.

In this specification, examples of alicyclic tertiary amines include N-methylpiperazine, N-methylpyrrolidine, 5-diazabicycio[4,3,0]nonan-5-ene, 1,4-diazabicyclo[2,2,2]octane, and the like.

In this specification, examples of aromatic amines include aniline, methylaniline, dimethylaniline, N,N-dimethylaniline, haloaniline, nitroaniline, and the like.

In this specification, examples of heterocyclic amines include pyridine, pyrimidine, piperazine, quinoline, imidazole, and the like.

For c) the fluoride, preferable examples of the Group 1 element of the periodic table represented by M in the formula: MF include H, Na, and K, with H being particularly preferable. That is, preferable examples of c) the fluoride include HF.

The Group 1 element of the periodic table represented by M may be a cation.

Examples of d) the halogenated fluorine compound include $IF_5$, $BrF_3$, and $ClF_3$.

More preferable examples of the halogenated fluorine compound include $IF_5$ and $BrF_3$.

Particularly preferable examples of the halogenated fluorine compound include $IF_5$.

These may be used singly or in a combination of two or more.

Preferable examples of e) the sulfur chloride include sulfur monochloride (SCl), disulfur dichloride ($S_2Cl_2$), and sulfur dichloride ($SCl_2$).

Preferable examples of the sulfur chloride include sulfur monochloride.

These may be used singly or in a combination of two or more.

In a preferable embodiment according to the present invention, a) the carbonyl compound containing a —C(O)— moiety,
d) the halogenated fluorine compound represented by the formula: $XF_n$, wherein X represents chlorine, bromine, or iodine, and n is a natural number of 1 to 5, and
e) the sulfur chloride, as well as
b) an amine and
c) a fluoride represented by the formula: MF, wherein M represents a Group 1 element of the periodic table, are mixed.

The upper limit of the amount of b) the amine used in the reaction of step A is preferably 2 equivalents, more preferably 1.5 equivalents, and still more preferably 1 equivalent in a molar ratio relative to the halogenated fluorine compound.

The lower limit of the amount of b) the amine used in the reaction of step A is preferably 0.5 equivalents, more preferably 0.8 equivalents, still more preferably 0.9 equivalents, and still even more preferably 1 equivalent in a molar ratio relative to the halogenated fluorine compound.

The amount of b) the amine used in the reaction of step A is preferably 0.5 to 2 equivalents, more preferably 0.8 to 1.2 equivalents, and still more preferably 0.9 to 1.1 equivalents in a molar ratio relative to the halogenated fluorine compound.

The upper limit of the amount of c) the fluoride used in the reaction of step A is preferably 9 equivalents, more preferably 7 equivalents, still more preferably 5 equivalents, and still even more preferably 3 equivalents in a molar ratio relative to the amine.

The lower limit of the amount of c) the fluoride used in the reaction of step A is preferably 2 equivalents, more preferably 2.5 equivalents, and still more preferably 3 equivalents in a molar ratio relative to the amine.

The amount of c) the fluoride used in the reaction of step A is preferably 2.5 to 9 equivalents, more preferably 2.5 to 7 equivalents, still more preferably 2.5 to 5 equivalents, and still even more preferably 3 to 5 equivalents in a molar ratio relative to the amine.

The upper limit of the amount of d) the halogenated fluorine compound used in the reaction of step A is preferably 3 equivalents, more preferably 2.2 equivalents, and still more preferably 1.8 equivalents in a molar ratio relative to e) the sulfur chloride.

The lower limit of the amount of the halogenated fluorine compound used in the reaction of step A is preferably 1 equivalent, and more preferably 1.5 equivalents in a molar ratio relative to the sulfur chloride.

The amount of the halogenated fluorine compound used in the reaction of step A is preferably 1 to 3 equivalents, more preferably 1.5 to 2.2 equivalents, and still more preferably 1.5 to 1.8 equivalents in a molar ratio relative to the sulfur chloride.

In step A, other substances may also be mixed in addition to a) the carbonyl compound, b) the amine, c) the fluoride, as well as d) the halogenated fluorine compound and e) the sulfur chloride, which are optionally used.

Examples of the other substances include reaction solvents.

Specific examples of the reaction solvents include dichloromethane, tetrachloroethane, chloroform, carbon tetrachloride, cyclohexane, and mixed solvents of two or more of these.

The amount of such other substances may be suitably determined according to the purpose of use.

In the production method of the present invention, a) the carbonyl compound, b) the amine, and c) the fluoride, as well as d) the halogenated fluorine compound and e) the sulfur chloride, which are optionally added, are introduced or added simultaneously or sequentially to the reaction system of step A.

Therefore, in mixing in step A, a) the carbonyl compound, b) the amine, and c) the fluoride, as well as d) the halogenated fluorine compound and e) the sulfur chloride, which are optionally added, are not necessarily present all together to be mixed.

More specifically, for example, 1 to 4 substances from among the 5 substances a) to e) may have undergone modification by chemical reaction etc. before the substance(s) other than the 1 to 4 substances are added to the reaction system of step A.

In step A, all or part of one or more substances a) to e) may be used in the form of a precursor thereof, a salt thereof, or a complex thereof.

In a preferable embodiment according to the present invention, b) the amine and c) the fluoride are used in the form of a salt thereof (a salt of an amine and hydrogen fluoride).

This salt can be used as all or part of b) the amine and c) the fluoride.

In other words, at least one member selected from the group consisting of b) the amine and c) the fluoride can also be used, in addition to this salt.

Specific examples of the salt (a salt of an amine and hydrogen fluoride) include a salt of a primary amine and hydrogen fluoride, a salt of a secondary amine and hydrogen fluoride, and a salt of a tertiary amine and hydrogen fluoride.

Preferable examples of a salt of an amine and hydrogen fluoride include a salt of aliphatic primary amine and hydrogen fluoride, a salt of aliphatic secondary amine and hydrogen fluoride, and a salt of aliphatic tertiary amine and hydrogen fluoride.

Examples of the aliphatic primary amine in the salt of aliphatic primary amine and hydrogen fluoride include methylamine, ethylamine, propylamine, butylamine, pentylamine, hexylamine, and the like.

Examples of the aliphatic secondary amine in the salt of aliphatic primary amine and hydrogen fluoride include dimethylamine, diethylamine, dipropylamine, dibutylamine, dipentylamine, dihexylamine, and the like.

Examples of the aliphatic tertiary amine in the salt of aliphatic tertiary amine and hydrogen fluoride include trimethylamine, triethylamine, diisopropylethylamine, tributylamine, N,N,N',N'-tetramethylethylenediamine, and the like.

Preferable examples of the "aliphatic (group)" in the "salt of aliphatic primary amine and hydrogen fluoride," "salt of aliphatic secondary amine and hydrogen fluoride," and "salt of aliphatic tertiary amine and hydrogen fluoride" include methyl, ethyl, and butyl, with ethyl and butyl being more preferable.

For example, the salt of an amine and hydrogen fluoride is preferably a salt of a tertiary amine and hydrogen fluoride, and more preferably a salt of aliphatic tertiary amine and hydrogen fluoride.

The salt of an amine and hydrogen fluoride may be, for example, a salt represented by the formula: $R_3N \cdot nHF$, wherein R, in each occurrence, is identical or different and represents (cyclo)alkyl (optionally substituted with one or more halogen atoms) or three Rs, taken together with the N to which they are attached, may form a nitrogen-containing heterocyclic ring optionally substituted with at least one (cyclo)alkyl group (optionally substituted with one or more halogen atoms); and n is a number of 1 to 9 (e.g., 1, 2, 3, 4, 5, 6, 7, 8, or 9).

This salt may also be, for example, a salt represented by the formula: $[R_3NH]^+[F(HF)_{n-1}]^-$, wherein R, in each occurrence, is identical or different and represents (cyclo)alkyl (optionally substituted with one or more halogen atoms) or three Rs, taken together with the N to which they are attached, may form a nitrogen-containing heterocyclic ring optionally substituted with at least one (cyclo)alkyl group (optionally substituted with one or more halogen atoms); and n is a number of 1 to 9 (e.g., 1, 2, 3, 4, 5, 6, 7, 8, or 9).

The salt of an amine and hydrogen fluoride is particularly preferably a salt of trimethylamine and hydrogen fluoride.

In another preferable embodiment according to the present invention, b) the amine, c) the fluoride, and d) the halogenated fluorine compound are used in the form of a complex of b) the amine, c) the fluoride, and d) the halogenated fluorine compound.

This complex can be used as all or part of b) the amine, c) the fluoride, and d) the halogenated fluorine compound.

In other words, at least one member selected from the group consisting of b) the amine, c) the fluoride, and d) the halogenated fluorine compound may also be used, in addition to the complex.

Preferable examples of the complex include an $IF_5$—HF— pyridine complex.

The $IF_5$—HF-pyridine complex is composed of (1) $IF_5$, (2) 1 mol of pyridine per mol of $IF_5$, and (3) 1 mol of HF per mol of $IF_5$.

$IF_5$-pyridine-HF is generally produced in accordance with the method disclosed in S. Hara, M. Monoi, R. Umemura, C. Fuse, Tetrahedron, 2012, 68, 10145-10150.

Specifically, $IF_5$-pyridine-HF is obtained by mixing $IF_5$ with pyridine-HF (pyridine 50 mol %, HF 50 mol %). Pyridine-HF (pyridine 50 mol %, HF 50 mol %) is obtained by adding pyridine to an equimolar amount of anhydrous HF.

The reaction temperature of step A is preferably room temperature.

The upper limit of the reaction temperature of step A is preferably 100° C. and more preferably 70° C.

The lower limit of the reaction temperature of step A is preferably −20° C. and more preferably 0° C.

The reaction temperature of step A is preferably −20° C. to 100° C., and more preferably 0° C. to 70° C.

An excessively low reaction temperature may cause insufficient reaction of step A.

An excessively high reaction temperature is disadvantageous in view of costs and may cause undesirable reaction.

The reaction of step A may be stopped, as desired, by adding $NaHCO_3$ etc.

The upper limit of the reaction time of step A is preferably 24 hours, more preferably 12 hours, and still more preferably 5 hours.

The lower limit of the reaction time of step A is preferably 1 minute, more preferably 10 minutes, and still more preferably 30 minutes.

The reaction time of step A is preferably 1 minute to 24 hours, more preferably 10 minutes to 12 hours, and still more preferably 30 minutes to 5 hours.

An excessively short reaction time may cause insufficient reaction of step A.

An excessively long reaction time is disadvantageous in view of costs and may cause undesirable reaction.

The difluoromethylene compound containing a —$CF_2$— moiety produced in step A may be purified, as desired, by conventional purification methods, such as concentration, extraction, distillation, solvent washing, column treatment, and combinations thereof.

Step A may comprise:
step A1 of reacting the halogenated fluorine compound (a) with the sulfur chloride (b); and
step A2 of reacting the carbonyl compound represented by formula (2) with the reaction product of step A1.

Step A1 and step A2 can be performed sequentially or simultaneously.

The reaction temperature of step A1 is preferably room temperature.

The upper limit of the reaction temperature of step A1 is preferably 100° C. and more preferably 70° C.

The lower limit of the reaction temperature of step A1 is preferably −50° C., more preferably −30° C., and still more preferably −20° C.

The reaction temperature of step A1 is preferably −20° C. to 100° C., and more preferably 0° C. to 70° C.

An excessively low reaction temperature may cause insufficient reaction of step A1.

An excessively high reaction temperature is disadvantageous in view of costs and may cause undesirable reaction.

Step A1 may be carried out in the presence or absence of a reaction solvent.

Specific examples of the reaction solvent include dichloromethane, tetrachloroethane, chloroform, carbon tetrachloride, cyclohexane, and mixed solvents of two or more of these.

The reaction product obtained in step A1 may be separated or purified, as desired, by using a conventional method, such as extraction, before subjecting the reaction product to step A2. Alternatively, the reaction product obtained in step A1 may be suitably used directly in step A2.

The upper limit of the reaction time of step A1 is preferably 24 hours, more preferably 12 hours, and still more preferably 5 hours.

The lower limit of the reaction time of step A1 is preferably 1 minute, more preferably 10 minutes, and still more preferably 30 minutes.

The reaction time of step A1 is preferably 1 minute to 24 hours, more preferably 10 minutes to 12 hours, and still more preferably 30 minutes to 5 hours.

An excessively short reaction time may cause insufficient reaction of step A1.

An excessively long reaction time is disadvantageous in view of costs and may cause undesirable reaction.

The reaction temperature of step A2 is preferably room temperature.

The upper limit of the reaction temperature of step A2 is preferably 100° C. and more preferably 70° C.

The lower limit of the reaction temperature of step A2 is preferably −20° C. and more preferably 0° C.

The reaction temperature of step A2 is preferably −20° C. to 100° C., and more preferably 0° C. to 70° C.

An excessively low reaction temperature may cause insufficient reaction of step A2.

An excessively high reaction temperature is disadvantageous in view of costs and may cause undesirable reaction.

Step A2 may be carried out in the presence or absence of a reaction solvent.

Specific examples of the reaction solvent include dichloromethane, tetrachloroethane, chloroform, carbon tetrachloride, cyclohexane, and mixed solvents of two or more of these.

The upper limit of the reaction time of step A2 is preferably 48 hours, more preferably 24 hours, even more preferably 10 hours, and still even more preferably 5 hours.

The lower limit of the reaction time of step A2 is preferably 5 minute, more preferably 30 minutes, and still more preferably 1 hour.

The reaction time of step A2 is preferably 5 minutes to 48 hours, more preferably 30 minutes to 24 hours, still more preferably 1 hour to 10 hours, and even more preferably 1 to 5 hours.

An excessively short reaction time may cause insufficient reaction of step A2.

An excessively long reaction time is disadvantageous in view of costs and may cause undesirable reaction.

Step A1 and step A2 above may be performed in one pot. In this embodiment, a complex formed of b) the amine, c) the HF, and d) the halogenated fluorine compound can be used.

In one embodiment of the present invention, step A1 and step A2 are performed sequentially.

More specifically, the reaction of step A2 above can be initiated after the completion of the reaction of step A1 above.

In one embodiment of the present invention, step A1 and the step A2 are performed simultaneously.

More specifically, the reaction of step A2 above can be initiated before the reaction of step A1 above is completed.

In this embodiment, a complex formed of b) the amine, c) the HF, and d) the halogenated fluorine compound can be used.

The production method of the present invention can be conducted, for example, by placing a complex of b) the amine, c) the HF, and d) the halogenated fluorine compound, as well as a) the carbonyl compound, in a container, followed by addition of e) the sulfur chloride to the container.

For example, the production method of the present invention may also be conducted by allowing the reaction of step A1 to proceed in a first container, and allowing the reaction of step A2 to proceed by placing a) the carbonyl compound in a second container, connecting the first container and the second container to allow the substances contained in these containers to be brought into contact with each other.

The difluoromethylene compound produced by using the production method of the present invention can be purified, as desired, by a known method, such as extraction.

The conversion percentage of the production method of the present invention is preferably 50% or more, more preferably 70% or more, and still more preferably 90% or more.

According to the production method of the present invention, the difluoromethylene compound is produced in a yield of preferably 30% or more, more preferably 50% or more, and still more preferably 70% or more.

According to the production method of the present invention, the difluoromethylene compound is produced with a selectivity of preferably 50% or more, more preferably 60% or more, and still more preferably 70% or more.

Composition

The present invention also provides a difluoromethylene compound containing a —$CF_2$— moiety, and a composition comprising a chlorofluoromethylene compound containing a —CHI—CFCl— moiety.

Just to note, the term "chlorofluoromethylene" in the chlorofluoromethylene compound refers to the —CFCl— moiety in the —CHI—CFCl— moiety.

According to the production method of the present invention, a difluoromethylene compound containing a —$CHX^1$—$CFX^2$— moiety can also be produced, in addition to the difluoromethylene compound.

Therefore, the composition can be produced by using the production method of the present invention described above.

EXAMPLES

The present invention is described below in more detail with reference to Examples. However, the present invention is not limited to these Examples.

Example 1

2.0 mL (3.4 g: 25 mmol) of $S_2Cl_2$ was placed in a first autoclave (volume: 200 mL). After being hermetically sealed, the autoclave was cooled to −78° C., and the pressure was reduced. Thereafter, 3.4 mL (11 g, 50 mmol) of $IF_5$ was slowly added thereto dropwise. The autoclave was removed from a dry ice-acetone bath and left to stand at room temperature. Forty minutes later, the temperature reached about 0° C., and the pressure was increased to 0.6 MPa, and thereby gas generation was confirmed.

2.9 g (25 mmol) of ethyl pyruvate, 0.5 g (25 mmol) of hydrogen fluoride, and 5 mL of dichloromethane were placed in a second autoclave. After the autoclave was cooled to −78° C., and the internal pressure of the autoclave was reduced, this autoclave was connected to the first autoclave to allow the generated gas to be transferred. When the pressure of the first autoclave decreased to the atmospheric pressure or less, the valve was closed, and stirring was performed in the second autoclave at room temperature overnight.

The reaction solution was collected and quenched with NaHCO$_3$, followed by GC analysis. The conversion percentage was 100%, and CH$_3$CF$_2$CO$_2$Et was obtained with a selectivity of 55%.

Example 2

6.6 g (20 mmol) of an IF$_5$-HF-pyridine complex was placed in an autoclave (volume: 200 mL), to which 5 mL of dichloromethane was added to prepare a solution. While stirring this solution, 2.32 g (20 mmol) of ethyl pyruvate was added thereto, followed by dropwise addition of 0.8 ml (10 mmol) of S$_2$Cl$_2$. The temperature rise or gas generation was not observed. After being hermetically sealed, the autoclave was gradually heated to 70° C. in an oil bath. Twenty minutes later, the pressure was increased to 0.4 MPa, and thereby gas generation was confirmed. After heating was stopped, and the resulting product was stirred at room temperature for 1 hour, the generated gas was released, and the reaction product mixture was collected. The reaction product mixture was diluted with dichloromethane and washed twice with a potassium sulfite aqueous solution. This solution was dried over magnesium sulfate and analyzed by GC and $^{19}$F-NMR. The conversion percentage was 100%, and CH$_3$CF$_2$CO$_2$Et was obtained with a selectivity of 73%.

Example 3

3.85 g (12 mmol) of an IF$_5$—HF-pyridine complex was placed in an autoclave (volume: 200 mL), to which 2.5 mL of dichloromethane was added to prepare a solution. While stirring, 1.06 g (10 mmol) of benzaldehyde was added to the solution, followed by dropwise addition of 0.48 mL (6 mmol) of S$_2$Cl$_2$. The temperature rise or gas generation was not observed.

After being hermetically sealed, the autoclave was gradually heated to 70° C. in an oil bath. Twenty minutes later, the pressure was increased to 0.3 MPa, and thereby gas generation was confirmed.

After stirring for 3 hours, the generated gas was released, and the reaction product mixture was collected. The reaction product mixture was diluted with dichloromethane and washed twice with a potassium sulfite aqueous solution.

This solution was dried over magnesium sulfate and analyzed by GC and $^{19}$F-NMR. The conversion percentage was 54% and PhCF$_2$H was obtained with a selectivity of 73%.

Example 4

3.85 g (12 mmol) of an IF$_5$—HF-pyridine complex was placed in an autoclave (volume: 200 mL), to which 2.5 mL of dichloromethane was added to prepare a solution. While stirring, 1.9 mL (10 mmol) of 2-decanone was added to the solution, followed by dropwise addition of 0.48 mL (6 mmol) of S$_2$Cl$_2$. The temperature rise or gas generation was not observed.

After being hermetically sealed, the autoclave was gradually heated to 70° C. in an oil bath. Twenty minutes later, the pressure was increased to 0.2 MPa, and thereby gas generation was confirmed.

After stirring for 3 hours, the generated gas was released, and the reaction product mixture was collected. The reaction product mixture was diluted with dichloromethane and washed twice with a potassium sulfite aqueous solution. This solution was dried over magnesium sulfate and analyzed by GC and $^{19}$F-NMR. The conversion percentage was 91%, and CH$_3$CF$_2$(CH$_2$)$_6$CH$_3$ was obtained with a selectivity of 11%.

Example 5

3.85 g (12 mmol) of an IF$_5$—HF-pyridine complex was placed in an autoclave (volume: 200 mL), to which 2.5 mL of dichloromethane was added to prepare a solution. While stirring, 1.03 mL (10 mmol) of cyclohexanone was added to the solution, followed by dropwise addition of 0.48 mL (6 mmol) of S$_2$Cl$_2$. The temperature rise or gas generation was not observed.

After being hermetically sealed, the autoclave was gradually heated to 70° C. in an oil bath. Twenty minutes later, the pressure was increased to 0.3 MPa, and thereby gas generation was confirmed.

After stirring at 40° C. for 12 hours, the generated gas was released, and the reaction product mixture was collected. The reaction product mixture was diluted with dichloromethane and washed twice with a potassium sulfite aqueous solution.

This solution was dried over magnesium sulfate and analyzed by GC and $^{19}$F-NMR. The conversion percentage was 84%, and 1,1-difluorocyclohexane was obtained with a selectivity of 27%.

Example 6

7.70 g (24 mmol) of an IF$_5$—HF-pyridine complex was placed in an autoclave (volume: 200 mL), to which 10 mL of dichloromethane was added to prepare a solution. While stirring, 1.36 g (10 mmol) of p-toluic acid was added thereto, followed by dropwise addition of 0.96 mL (12 mmol) of S$_2$Cl$_2$. The temperature rise or gas generation was not observed.

After being hermetically sealed, the autoclave was gradually heated to 70° C. in an oil bath. Twenty minutes later, the pressure was increased to 0.7 MPa, and thereby gas generation was confirmed.

The temperature was gradually increased to 120° C., and stirring was performed for 12 hours. Thereafter, the generated gas was released, and the reaction product mixture was collected.

The reaction product mixture was diluted with dichloromethane and washed twice with a potassium sulfite aqueous solution.

This solution was dried over magnesium sulfate and analyzed by GC and $^{19}$F-NMR. The conversion percentage was 100%, an acid-4-methylbenzoyl fluoride was obtained with a selectivity of 81%, and 1-(trifluoromethyl)-4-methylbenzene was obtained with a selectivity of 19%.

The invention claimed is:

1. A method for producing a difluoromethylene compound containing a —CF$_2$— moiety, the method comprising
   step A of mixing:
   a) a carbonyl compound containing a —C(O)— moiety;
   b) optionally an amine;
   c) a fluoride represented by the formula: MF, wherein M represents a Group 1 element of the periodic table;
   d) a halogenated fluorine compound represented by the formula: XF$_n$, wherein X represents chlorine, bromine, or iodine, and n is a natural number of 1 to 5; and e) sulfur monochloride, disulfur dichloride or sulfur dichloride.

2. The production method according to claim 1, wherein the difluoromethylene compound containing a —CF$_2$— moiety is a difluoromethylene compound represented by formula (1):

$$R^{11}\text{—}CF_2\text{—}R^{12} \qquad (1),$$

wherein:
$R^{11}$ represents $R^{21}$ or fluorine,
$R^{12}$ represents $R^{22}$ or fluorine, and
(A):
$R^{21}$ and $R^{22}$ are identical or different, and each represents
(a) hydrogen,
(b) hydroxyl, or
(c) an organic group, or
(B):
$R^{21}$ and $R^{22}$ are identical or different, and each represents
(a) hydrogen, or
(c) an organic group,
wherein $R^{21}$ and $R^{22}$, taken together with the —CF$_2$— moiety to which they are attached, may form a ring,
with the proviso that
(i) neither $R^{11}$ nor $R^{12}$, and neither $R^{21}$ nor $R^{22}$, is an organic group bonded via —O—, and
(ii) the carbonyl compound is a carbonyl compound represented by formula (2):

$$R^{21}\text{—}C(O)\text{—}R^{22} \qquad (2),$$

wherein the symbols in the formula are as defined above.

3. The production method according to claim 1, wherein d) the halogenated fluorine compound is ifs.

4. The production method according to claim 1, wherein the method comprises mixing b) the amine and c) the fluoride.

5. The production method according to claim 4, wherein b) the amine and c) the fluoride are used in the form of a salt of b) the amine and c) the fluoride.

6. The production method according to claim 1, wherein b) the amine, c) the fluoride, and d) the halogenated fluorine compound are used in the form of a complex of b) the amine, c) the fluoride, and d) the halogenated fluorine compound.

7. The production method according to claim 1, wherein c) the fluoride is HF.

8. The production method according to claim 1, wherein step A comprises:
  step A1 of reacting d) the halogenated fluorine compound with e) the sulfur monochloride, disulfur dichloride or sulfur dichloride; and
  step A2 of reacting a) the carbonyl compound with a reaction product of step A1.

9. The production method according to claim 8, wherein step A1 and step A2 are performed in one pot.

10. The production method according to claim 9, wherein step A1 and step A2 are performed sequentially.

11. The production method according to claim 9, wherein step A1 and step A2 are performed simultaneously.

* * * * *